United States Patent [19]

Maxwell

[11] Patent Number: 5,026,648
[45] Date of Patent: * Jun. 25, 1991

[54] MICROBIAL CULTURE HAVING CATECHOL 1,2-OXYGENASE ACTIVITY

[75] Inventor: Peter C. Maxwell, New Providence, N.J.

[73] Assignee: Celgene Corporation, Warren, N.J.

[*] Notice: The portion of the term of this patent subsequent to Oct. 19, 1999, has been disclaimed.

[21] Appl. No.: 818,707

[22] Filed: Jan. 14, 1986

Related U.S. Application Data

[63] Continuation of Ser. No. 516,088, Jul. 22, 1983, Pat. No. 4,731,328, which is a continuation-in-part of Ser. No. 287,344, Jul. 27, 1981, abandoned.

[51] Int. Cl.$^5$ .......................... C12N 1/20; C12N 9/04; C12P 7/44
[52] U.S. Cl. ................. 435/253.3; 435/142; 435/190; 435/877
[58] Field of Search .................. 435/142, 172.1, 253, 435/877, 190, 253.3

[56] References Cited

U.S. PATENT DOCUMENTS 4,355,107 10/1982 Maxwell ............................ 435/877

OTHER PUBLICATIONS

Gottschalk, "Bacterial Metabolism", Springer-Verlag, N.Y., 1979, pp. 126-131.

Vander Linden et al, "Microbial Oxidation of Hydrocarbons", Advances in Enzymology 27, pp. 506-516 (1965).

Ornston et al, "Isolation of Spontaneous Mutants of Pseudomonas ·Putida", Biochemical and Biophysical Research Communications 36(1), pp. 179-184 (1969).

Condon et al, "Cold Sensitive Mutation of Pseudomonas Putida Affecting Enzyme Synthesis at Low Temperatures", Journal of Bacteriology 94(6), pp. 1970-1981 (1967).

Kleinzeller et al, Chem. Listy 46, pp. 300-302 (1952), Chem. Abst. 47:4290a.

Hayaishi et al. Journal of the American Chemical Society 77, pp. 5450-5451 (1955).

Primary Examiner—Jacqueline Stone
Attorney, Agent, or Firm—Mathews, Woodbridge, & Collins

[57] ABSTRACT

This invention provides novel strains of microorganisms (e.g., *Pseudomonas putida* Biotype A) which are capable of converting substrates such as toluene or catechol to muconic acid quantitatively by the ortho (catechol 1,2-oxygenase) pathway.

Muconate lactonizing enzyme is not induced in the microorganism, thereby permitting the muconic acid to be produced and accumulated in a quantity greater than one gram of muconic acid per liter of bioconversion medium.

2 Claims, 1 Drawing Sheet

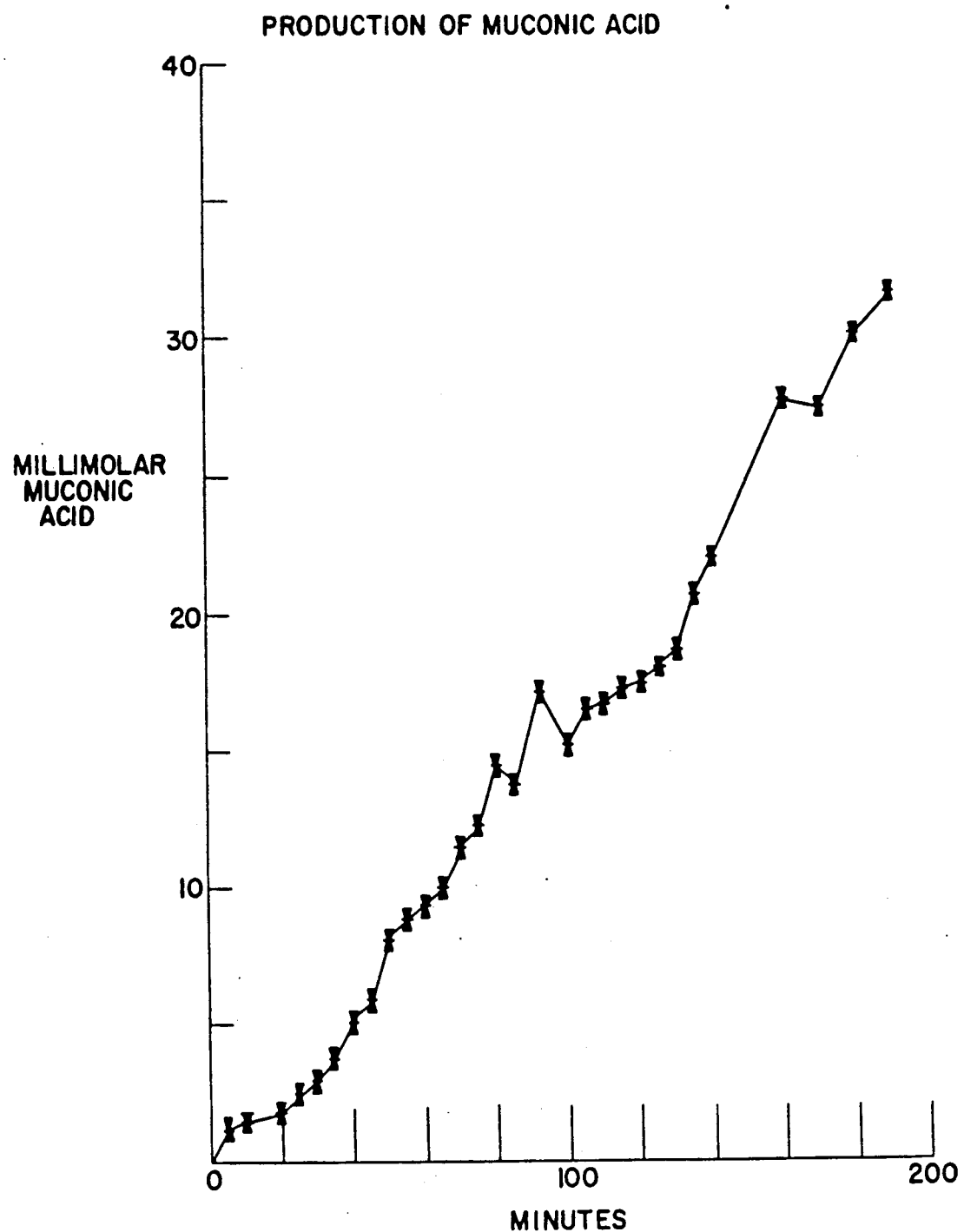

MICROBIAL CULTURE HAVING CATECHOL 1,2-OXYGENASE ACTIVITY

This patent application is a continuation of pending patent application Ser. No. 516,088, filed July 22, 1983; now U.S. Pat. No. 4,731,328 which is a continuation-in-part of patent application Ser. No. 287,344, filed July 27, 1981, now abandoned.

The present invention is related to the subject matter of U.S. Pat. No. 4,355,107 which issued Oct. 19, 1982.

BACKGROUND OF THE INVENTION

Adipic acid is an important commodity in the chemical industry, particularly or consumption as a commoner in the synthesis of polymers. Adipic acid can be obtained by oxidation of cyclohexane or cyclohexanol. Another prospective method is by the hydrogenation of muconic acid, which is a diolefinically unsaturated adipic acid derivative:

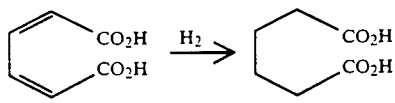

A potentially convenient source of muconic acid is by the microbiological oxidation of various hydrocarbon substrates. Microbiological oxidation of hydrocarbons is reviewed in Applied Microbiology, 9(5), 383(1961) and in "Advances in Enzymology", 27, 469–546(1965) by Interscience Publishers.

U.S. Pat. No. 3,383,289 describes a process for producing a methyl-substituted muconic acid and/or 2,3-dihydroxybenzoic acid which involves subjecting a $C_7$–$C_{10}$ methylbenzene having 1–4 methyl groups and at least two consecutive unsubstituted ring carbon atoms in the presence of a nutrient medium and under fermentation conditions to the action of an orthodihydroxylating and nondecarboxylating strain of Nocardia.

The Journal of Biological Chemistry, 241(16), 3776 (1966) reports the conversion of catechol and protocatechuate to β-ketoadipate by *Pseudomonas putida*. The conversion of catechol proceeds by the ortho pathway via a muconic acid intermediate:

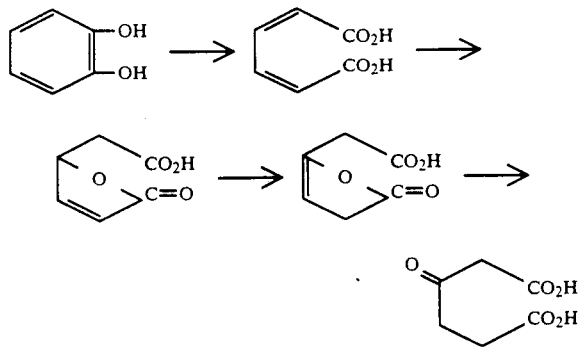

The chemical structures illustrated in the reaction scheme are catechol, muconic acid, muconolactone, β-ketoadipate enollactone and β-ketoadipate, respectively.

In the Journal Of Bacteriology, 134, 756(1978) there is reported a study of the ubiquity of plasmids in coding for toluene and xylene metabolism in soil bacteria. One of the mutant strains of *Pseudomonas putida* isolated had the ability to metabolize toluene via benzyl alcohol, benzaldehyde, benzoic acid and catechol by the ortho pathway through β-ketoadipate to biomass and carbon dioxide.

The enzymes functioning in the toluene metabolism by the ortho pathway included toluene mono-oxygenase, benzyl alcohol dehydrogenase, benzaldehyde dehydrogenase, benzoate oxygenase, dihydrodihydroxybenzoate dehydrogenase, catechol 1,2-oxygenase and muconate lactonizing enzyme. The subsequently formed β-ketoadipate was further assimilated to biomass and carbon dioxide. The mutant strains that metabolized toluene via the ortho pathway did not accumulate muconic acid, since the said muconic acid metabolite was further transformed in the presence of muconate lactonizing enzyme.

No known naturally occurring microorganisms (e.g., *Pseudomonas putida*) are known that metabolize an aromatic substrate such as toluene by the ortho pathway via muconic acid and β-ketoadipate. Wild strains metabolize aromatic hydrocarbon substrates by the meta pathway via 2-hydroxymuconic semialdehyde instead of a muconic acid intermediate. Catechol 2,3-oxygenase is functional rather than catechol 1,2-oxygenase.

Thus, the potential of microbiological oxidation of an aromatic substrate such as toluene as a convenient source of muconic acid requires the construction of mutant strains of microorganisms which (1) metabolize an aromatic substrate via catechol by means of the ortho pathway, (2) allow the accumulation of muconic acid without its further assimilation, and (3) contain catechol 1,2-oxygenase which is not inhibited by accumulated muconic acid in a bioconversion medium.

Accordingly, it is an object of this invention to provide a process for construction of novel strains of microorganisms which metabolize catechol or a catechol-precursor by the ortho pathway to accumulated muconic acid.

It is another object of this invention to provide novel strains of pseudomonads which metabolize toluene or other benzoic acid-precursor to muconic acid quantitatively, with an accumulation of greater than one gram of muconic acid per liter of bioconversion medium.

Other objects and advantages of the present invention shall become apparent from the accompanying description and examples.

DESCRIPTION OF THE INVENTION

One or more objects of the present invention are accomplished by the provision of a process for the construction of novel microorganism strains which comprises (1) culturing a microorganism species selectively to provide strain A1 which metabolizes an aromatic substrate selected from toluene and other catechol-precursors by the ortho pathway via catechol to muconic acid, and which subsequently metabolizes the resultant muconic acid via β-ketoadipate to biomass and carbon dioxide; (2) continuously and selectively culturing strain A1 for rapid growth on the aromatic substrate as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a nonselective carbon source and excess benzoate; (6) isolating cells from single small colonies, and culturing the cell isolates and selecting a strain A3, wherein strain A3 converts the aromatic substrate to accumulated muconic acid.

BRIEF DESCRIPTION OF THE DRAWING

The FIGURE shows muconic acid production by *Pseudomonas putida* Biotype A, ATCC 31916.

The above construction procedure is generally applicable to microorganisms that metabolize catechol-precursor type of organic substrates such as ethylbenzene, styrene, benzyl alcohol or benzaldehyde. The procedure can be modified to accommodate microorganisms that metabolize other aromatic substrates such as benzene, naphthalene, phenol, salicylic acid, aniline, anthranilic acid, and the like, as disclosed in copending patent application Ser. No. 513,231, filed July 22, 1983, now U.S. Pat. No. 4,588,688, incorporated herein by reference.

The starting microorganism can be any organism capable of growth on the selected aromatic substrate and possessing active catechol 1,2-oxygenase, e.g., a pseudomonad. A variety of naturally occurring organisms have these traits including some members of the species *Pseudomonas putida, Pseudomonas aeruginosa, Pseudomonas fluorescens;* some members of the genera Azotobacter and Nocardia; and a number of unclassified fungi (both molds and yeasts).

In another embodiment, this invention provides biologically pure microbial cultures which possess catechol 1,2-oxygenase enzyme with activity that is not inhibited in the presence of a low level of muconic acid in a bioconversion medium. A present invention microorganism converts catechol quantitatively to accumulated muconic acid. "Biologically pure" refers to a microbial culture which does not contain more than about one cell per $10^5$ cells which is not essentially identical to the predominate strain cell population.

Preferred microorganisms are those which have been modified by a construction procedure to possess a novel combination of enzymes which include catechol 1,2-oxygenase with activity that is not inhibited in the presence of a low level up to about one gram or more of muconic acid per liter of bioconversion medium.

This invention provides microbial cultures each of which has the following characteristics:
  (a) possesses active benzoate dioxygenase;
  (b) possesses active 1,2-dihydrodihydroxybenzoate dehydrogenase;
  (c) lacks active catechol 2,3-oxygenase;
  (d) does not grow on benzoate or halobenzoate;
wherein the microbial culture is capable of metabolizing catechol quantitatively to an accumulated quantity of muconic acid greater than about one gram per liter of a bioconversion medium.

In another embodiment, this invention provides microbial cultures each of which exhibits the following enzymatic activities:
  (a) possesses active benzoate dioxygenase and 1,2-dihydrodihydroxybenzoate dehydrogenase and catechol 1,2-oxygenase;
  (b) lacks active catechol 2,3-oxygenase; and
  (c) does not grow on benzoate or monohalobenzoate;
wherein the microbial culture is capable of metabolizing an aromatic substrate selected from toluene and other catechol-precursors by the ortho pathway quantitatively to an accumulated quantity of muconic acid greater than about one gram per liter of a bioconversion medium. "Quantitative" refers to a conversion selectivity to muconic acid of at least about 90 percent.

Further illustrative of the invention microorganisms are constructed biologically pure strains of fluorescent Pseudomonads each of which has the following characteristics:
  (a) possesses active benzoate dioxygenase;
  (b) possesses active 1,2-dihydrodihydroxybenzoate dehydrogenase;
  (c) possesses catechol 1,2-oxygenase with activity that is not inhibited in the presence of any low level quantity of muconic acid up to about one gram per liter of a bioconversion medium;
  (d) lacks active muconate lactonizing enzyme;
  (e) lacks active catechol 2,3-oxygenase;
  (f) does not grow on benzoate or monohalobenzoate (e.g., monochlorobenzoate); and
  (g) cells are rod shaped, vigorously motile and polarly flagellated.

A novel strain of *Pseudomonas putida* Biotype A, constructed in accordance with the present invention and having the above recited modified characteristics, has been deposited with the American Type Culture Collection and has been designated as ATCC No. 31916.

In a further embodiment, this invention provides a process for the production of muconic acid which comprises feeding toluene or other catechol-precursor aromatic substrate to a bioconversion medium containing a novel strain of fluorescent Pseudomonas, e.g., a strain having an enzyme profile similar to that of ATCC No. 31916 and its mutants.

The rate of aromatic substrate conversion typically is at least about 30 milligrams of muconic acid produced per dry weight gram of cells per hour. The conversion of aromatic substrate proceeds readily at a dry weight cell concentration of 50 grams per liter, with a resultant muconic acid production rate of 1.5 grams per liter per hour.

Under optimal conditions, the muconic acid accumulation limit can approach up to about 50 grams of muconic acid per liter of bioconversion medium. The microbiological oxidation process normally is conducted at ambient temperatures up to about 31° C.

The ortho pathway (also known as the β-ketoadipate pathway or the catechol 1,2-oxygenase pathway) has been studied in *Pseudomomonas putida, Acinebacter calcoaceticus,* and *Alcaligenese eutrophus.* Research effort for the most part has concentrated on the metabolism of benzoate. The organisms are ubiquitous in nature and are easily isolated by enrichment culture on benzoate containing media. The initial reaction in the metabolism of benzoate is transport of the molecule into the cell followed by conversion of benzoate via benzoate dioxygenase and 1,2-dihydrodihydroxybenzoate dehydrogenase to catechol. The series of enzymes which convert catechol to β-ketoadipate constitute the ortho pathway proper. Catechol 1,2-oxygenase is the enzyme responsible for the conversion of catechol to muconic acid as described above.

Nature 188 560(1960) describes the meta pathway (also known as the 2,3-oxygenase pathway) for the metabolism of catechol and its precursors to carbon dioxide and cell carbon. The first intermediate after catechol is the intensely yellow 2-hydroxymuconic semialdehyde. Because the rate limiting reaction in this pathway occurs at some point after the semialdehyde formation, the compound is excreted into the medium when induced cells are exposed to catechol. This phenomenon serves as a basis for differentiating between cells using either the ortho or the meta pathway.

The microorganisms growing at the expense of benzoate via the ortho pathway grow at an appreciably higher rate than microorganisms growing on benzoate via the meta pathway, i.e., 50 minutes versus 210 minutes per doubling. A microorganism capable of metabolizing toluene via the ortho pathway therefore appears to have a decided selective advantage.

A novel mutant strain of the present invention (e.g., *Pseudomonas putida* Biotype A, strain ATCC No. 31,916) has characteristics which are unique for the microbiological conversion of toluene or other benzoic acid-precursor or catechol for the production and accumulation of muconic acid at an exceptional rate and concentration.

First, the parent microorganism is capable of growing at a rapid rate, e.g., a growth doubling time of about 1.5 hours on toluene.

Second, the mutant microorganism metabolizes toluene or other benzoic acid-precursor by the ortho pathway via catechol cleavage by the action of catechol 1,2-oxygenase. Concomitantly, no active catechol 2,3-oxygenase is induced in the microorganism culture.

Third, the catechol 1,2-oxygenase activity is not repressed or inhibited by the presence of a low level of muconic acid, e.g., a level of up to about one gram or more of muconic acid per liter of bioconversion medium. This permits the accumulation of muconic acid at a level which is higher than about one gram/liter of bioconversion medium.

Fourth, the ortho pathway series of conversion reactions is blocked subsequent to the formation of the muconic acid from catechol. The mutant microorganism lacks the presence of active muconate lactonizing enzyme. Hence, the muconic acid is able to accumulate as it is produced, i.e., the muconic acid accumulates up to a level of about 50 grams per liter of bioconversion medium. No microorganism reported in the literature is known to exhibit the ability to produce and accumulate muconic acid to these levels from an aromatic substrate.

Microbial cultures provided by the present invention have an inherent genome characteristic in common, i.e., each microbial culture is capable of bio-oxidizing catechol or a catechol-precursor by the ortho pathway to an accumulated quantity of muconic acid in a bioconversion system. Included in the invention microbial cultures are mutant strains which are acidophilic, i.e., they are capable of expressing their enzymatic properties in a bioconversion medium having a pH less than about 5, such as strains of *Thiobacillus acidophillus* which have been modified in accordance with a present invention construction procedure.

Microorganism Construction Procedure

In accordance with the present invention, a procedure has been developed to isolate a strain of organism which rapidly converts toluene or other benzoic acid-precursor to accumulated muconic acid. The first step is to isolate a mutant preferably of an original pseudomonad type isolate which grows on toluene or other catechol-precursor via the ortho pathway, i.e., the pathway in which muconic acid is an intermediate.

The original isolate is first made constitutive for growth on m-toluic acid. This first strain is then subjected to a cycle designed to eliminate the meta pathway and select for cells which have retained the ability to grow on toluene or other selected benzoic acid-precursor substrate. Cells are first grown from low dilution on benzoic acid. These cells are transferred to medium containing m-toluic acid as the sole source of carbon. After one hour, the antibiotics penicillin and D-cycloserine respectively are added at concentrations of 12 and 0.1/mg/ml and the incubation is continued for four to six hours. After the incubation, the cells are washed and transferred at a 50:1 dilution to medium containing the selected substrate as the sole sources of carbon. Visible growth occurs in approximately thirty-six hours.

When plated on agar containing benzoate a mixture of small and large colonies are formed. Virtually all of the large colonies metabolize the selected substrate via the ortho pathway, thus producing muconic acid as an intermediate. This second strain, characterized by growth on the selected substrate via the ortho pathway, does not possess an active catechol 2,3-oxygenase. Its doubling time on the selected substrate is approximately two to three hours.

The second strain is then subjected to selection for a rapid growth rate by being continuously cultured on the substrate as the sole source of carbon. Once the culture has stabilized at a doubling time of approximately four hours, the dilution rate is increased to require a doubling time of three hours. This process is repeated until the cells are growing with a doubling time of one to two hours. This third strain differs from its parent at least in its being constitutive for catechol 1,2-oxygenase.

The third strain converts the selected substrate to muconic acid but also converts muconic acid to biomass and carbon dioxide. To obtain a strain which accumulates muconic acid, it is necessary to isolate cells lacking a functional muconate lactonizing enzyme. The third strain is grown overnight on the selected substrate. These cells are transferred to media containing benzoic acid as the sole source of carbon. After one hour, penicillin and D-cycloserine are added and the incubation is continued for four to six hours. After the incubation, the cells are harvested, washed and transferred at a 500:1 dilution to medium containing p-hydroxybenzoate as the sole source of carbon. Cells grown overnight on p-hydroxybenzoate are transferred to medium containing benzoate as the sole source of carbon and the enrichment cycle is repeated. After six cycles, the survivors are plated on agar containing 5 mM benzoic acid and 0.5 mM succinic acid. On this medium, cells unable to metabolize benzoate form small colonies.

The single small colonies are picked and cultured, and after induction with the selected substrate, checked for their ability to produce muconate. A strain is selected which exhibits an ability to convert the selected substrate to muconic acid in an efficient manner.

The following examples are further illustrative of the present invention. The components and specific ingredients are presented as being typical, and various modifications can be derived in view of the foregoing disclosure within the scope of the invention.

The basal salts medium employed for all of the series had the following composition:
50 mM of $Na_2HPO_4$
100 mM of $KH_2PO_4$
17 mM of $(NH_4)_2SO_4$
1 mM of $MgSO_4$ 0.1 mM of $CaCl_2$
0.01 mM of $FeSO_4$ The medium had a pH of 6.2, and the original organism used in the Examples was constructed from a natural isolate.

For cultivation, carbon sources such as toluene were added aseptically prior to inoculation. Incubation conditions were in 250 ml shake flasks. Shaking was in a rotary shaker with temperature controlled at 28° C.

Toluene was delivered to the shake flasks either from an ethanol sterilized dialysis bag or from a 5 ml layer of paraffin wax in the bottom of the flask. In the latter case, molten paraffin was pipetted into the flask, the flask was autoclave sterilized, and while still hot, toluene was added and mixed with the paraffin. After solidifying, the sterilized basal salts medium was added aseptically. In the case of the dialysis bags, the dialysis tubing was washed extensively and boiled to remove the glycerol which is incorporated as a plasticizer. Enough glycerol remained to support the growth of the microorganisms to the extent of approximately $6 \times 10^8$ cells per ml. In this system, only growth in excess of $7.5 \times 10^8$ ml was considered significant. The basal salts medium was capable of supporting growth of $3.3 \times 10^9$ cells per ml when there was an unlimited carbon source.

Growth was typically measured by determining the turbidity of the cell suspension in a Klett-Summerson Colorimeter using the #66 red filter. One Klett unit was found to be equivalent to $3 \times 10^6$ cells per ml or 17.5 mg wet weight per liter of 3.5 mg dry weight per liter.

Cultures were stored under liquid nitrogen.

EXAMPLE I

This Example illustrates the isolation of toluene oxidizing microorganisms.

Soil samples were collected from a variety of areas and added to medium plus paraffin containing toluene. After shaking at 28° C. for 24 hours growth was apparent in the medium. Strains were isolated by streaking on agar plates containing a vial of toluene in the lid. Colonies appeared on the agar after approximately 36 hours. The size of these colonies ranged from 1 to 5 mm. A representative sampling of these colonies was taken and cultures were stored under liquid nitrogen for long-term preservation.

A strain derived from one of the largest colonies was chosen for further work and designated MW 1000. This strain was identified as a *Pseudomonas putida* Biotype A on the basis of the following criteria:

(a) the cells were rod shaped, vigorously motile and polarly flagellated;
(b) cells grew well on benzoate and p-hydroxybenzoate;
(c) cell growth on benzoate induced the synthesis of carboxymuconate lactonizing enzyme and carboxymuconolactone decarboxylase but not protocatechuate oxygenase, a pattern of regulation characteristic only of the *Pseudomonas putida* Biotype A;
(d) the induced enzymes muconolactone isomerase, carboxy-muconate lactonizing enzyme, and carboxy-muconolactone decarboxylase were immunologically identical with those enzymes synthesized by *Pseudomonas putida* Biotype A, a saprophytic organism extensively studied in the literature.

A growth study of MW 1000 on toluene was conducted and it was found that the organism grew with a doubling time of approximately 3.5 hours and had a 5 hour lag period. Toluene grown MW 1000 consumed oxygen when presented with toluene, benzyl alcohol, benzaldehyde, m-toluate or catechol, but not with benzoate. With catechol the medium turned yellow indicating the production of excess 2-hydroxymuconic semialdehyde.

The presence of the meta pathway was confirmed by demonstration of 2,3-oxygenase activity in cell free extracts and a failure to demonstrate the 1,2-oxygenase. MW 1000 also oxidized benzoate via the meta pathway following induction with benzoate.

EXAMPLE II

This Example illustrates methods of constructing a strain of organism which oxidizes toluene via the ortho (catechol 1,2-oxygenase) pathway.

A series of mutants which metabolized toluene through the ortho pathway was constructed by first blocking the meta pathway and then isolating phenotypic revertants which had reacquired the ability to grow on benzoate. Strains possessing a meta pathway block were isolated after penicillin plus D-cycloserine enrichment for organisms which failed to grow on benzoate. Some fifty isolates were then spotted onto agar plates and incubated in the presence of toluene. Virtually all isolates reverted to growth on toluene. The plates were sprayed with 10 mM catechol and approximately 25% of the revertants were found not to produce 2-hydroxymuconic semialdehyde. None of the colorless revertants was found to possess an active catechol 2,3-oxygenase following induction with toluene.

It has been shown by Worsey and Williams, J. Bacteriol. 130, 1149 (1977) that growth on benzoate tends to cure a population of its TOL plasmid because the ortho pathway supports a higher growth rate. Since toluate can only be metabolized via the meta pathway, an alternative way to cure a population of its TOL plasmid is to use the penicillin plus D-cycloserine procedure to enrich for cells unable to grow on toluate.

Both these techniques were used in succession followed by counter-selection for growth on toluene. MW 1200 was first cultured on toluene. A small portion (0.05 ml) of this culture was transferred to 50 ml of benzoate medium. After growth on benzoate the cells were transferred to toluate and incubated for approximately one hour. Penicillin and D-cycloserine respectively were then added as described above and the incubation was continued for four to six hours. Cells were harvested, washed and transferred to a toluene containing medium. Growth on toluene required approximately 36 hours indicating an exceptionally low number of cells surviving the selection procedure.

After growth on toluene the cells were plated on benzoate agar and incubated for 48 hours, and a number of large colonies and a few small colonies were formed. After spraying with catechol it was found that all of the small colonies turned yellow (indicating the presence of the meta pathway) but none of the large colonies did. Large colonies were picked and cultured and it was found that, following growth on toluene, these strains contained no functional 2,3-oxygenase but were fully induced for the 1,2-oxygenase. These strains metabolized toluene by the ortho pathway. One isolate, designated MW 1210, was selected for further work. A growth study with MW 1210 showed a doubling time of approximately 2 hours.

The procedure developed for isolation of these mutants proved to be highly repeatable. The difference in colony size between meta oxidizers and ortho oxidizers was repeatable if plates were observed at 48 hours.

The frequency of the ortho oxidizers following this procedure has ranged from 50 to 100% of the total colonies on the plate. Enrichment from a single cycle, was on the order of $10^7$, although there was no means of assessing the concentration of mutants at the individual steps.

EXAMPLE III

This Example illustrates the construction of the novel *Pseudomonas putida* Biotype A strain ATCC No. 31916 of the present invention.

The strain of Example II was subjected to continuous cultivation with toluene as the sole source of carbon. Initially a dilution rate of 0.15 hours$^{-1}$ was employed. After the culture had stabilized, the dilution rate was increased successively to 0.25 hour$^{-1}$, 0.34 hour$^{-1}$, and 0.46 hour$^{-1}$. An isolate was made from the cells which dominated the culture at this latter dilution rate. This strain (MW 1211) was then used to construct a strain which accumulates muconic acid to greater than one gram per liter.

The above strain was cultured overnight in liquid medium on toluene as the sole source of carbon, then benzoate was added to a level of 5 mM and the incubation was continued for approximately 1 hour. Penicillin G and D-cycloserine were added at concentrations of 12 and 0.1 mg/ml respectively. The antibiotic incubation was continued for approximately 5 hours. The cells were then harvested by centrifugation and washed twice with sterile de-ionized water. An aliquot of these cells was then transferred to fresh medium containing 0.5 mM p-hydrobenzoate as a sole source of carbon, and the medium was incubated overnight. The procedure was repeated starting with induction with benzoate.

After 6 cycles those cells present in the culture after overnight growth on p-hydroxybenzoate were diluted and plated on an agar medium containing 0.5 mM succinate and 5.0 mM benzoate as sole sources of carbon. After 36 hours incubation the plate showed a mixture of large and small colonies. Cells from a number of small colonies were cultured in liquid medium, induced with toluene and tested for their ability to accumulate muconic acid. Of some 20 isolates one strain (MW 1211.1) was an accumulator of muconic acid.

EXAMPLE IV

This Example illustrates the conversion of toluene to muconic acid with an accumulation of greater than one gram of muconic acid per liter of conversion medium.

The microorganism employed was the ATCC No. 31916 strain of *Pseudomonas putida* Biotype A described in Example III.

Succinate was used as the source of carbon in the medium containing the ATCC No. 31,916 culture. After reaching a stationary phase, toluene was added to the medium to induce the appropriate enzymes. After about 2.5 hours, the cells were harvested by centrifugation and washed with buffer.

The conversion was performed in 150 mM of sodium potassium phosphate buffer at a pH of 7.5. The cell concentration was adjusted to 50 gm dry weight per liter. Toluene was added slowly in the vapor phase by bubbling the air or oxygen stream through a toluene reservoir. The concentration of muconic acid thereby produced was determined spectrophotometrically by the increase in absorbance at 260 nm. The muconic acid concentration rose to about 35-40 mM before the reaction becomes inhibited as shown in the FIGURE.

The identity of the muconic acid product was confirmed by high pressure liquid chromatography, melting point, and nuclear magnetic resonance.

EXAMPLE V

This Example illustrates the bioconversion of catechol to muconic acid, employing ATCC No. 31916 strain of *Pseudomonas putida* Biotype A.

Cells of ATCC No. 31,916 strain were inoculated into a Chemap 10 liter fermentor containing NO medium and 20 mM gluconate as a carbon source. The fermentor temperature was controlled at 29° C., and the agitation rate was 800 rpm and the air flow rate was 2.8 l/min.

After overnight incubation, the culture turbidity was 226 Klett units (0.79 g/l). At this point, feeds of acetic acid at a rate of 0.198 g/l/hr and catechol (from a 1M solution) at a rate of 2.22 mM/hr were begun. The acetic acid was added to ensure adequate carbon and energy for maintenance and enzyme synthesis (the absence of supplemental acetic acid yielded substantially the same results). A pH of 6.4 was controlled by automatic addition of 2N NaOH.

Muconic acid synthesis initiated immediately and continued at the same rate as catechol addition. The total quantity of catechol added was 400 mM and the reservoir was depleted in approximately 1023 minutes. The conversion of catechol to muconic acid was quantitative.

EXAMPLE VI

This Example illustrates the construction of an acidophilic microorganism capable of converting an aromatic substrate to muconic acid under low pH conditions.

Strain A2 (MW 1211) is patch mated with an auxotrophic strain of *Pseudomonas aruginosa* carrying a plasmid with chromosome-mobilizing activity, and which codes for antibiotic resistance (e.g., kanamycin resistance). Ex-conjugates are selected for growth on toluene plus 400 μg/ml kanamycin. Colonies of ex-conjugates are picked and patch mated with strain B1 (*Thiobacillus acidophillus*).

Ex-conjugates of this second mating are selected for growth on toluene at a pH of 3.5. Strain B2, a colony which grows under these acidic conditions, has the ability to grow on toluene via muconic acid at low pH. Strain B2 possesses a catechol 1,2-oxygenase which is not inhibited by a low level up to one gram of muconic acid per liter of bioconversion medium, and it possesses active muconate lactonizing enzyme.

In order to construct a mutant of strain B2 which is capable of producing and accumulating muconic acid from toluene, the same selection procedure is applied to Strain B2 as employed in Example III for deriving strain MW 1211.1 from strain MW 1211.

The resultant mutant obtained from the selection procedure, Strain B3, is capable of converting toluene (or other benzoic acid-precursor) at a pH of less than about 5 to an accumulated quantity of muconic acid greater than about one gram per liter of a bioconversion medium.

What is claimed is:

1. A microbial culture comprising a microorganism having the following characteristics:

(a) possesses active benzoate dioxygenase and 1,2-dihydrodihydroxybenzoate dehydrogenase and catechol 1,2-oxygenase;
(b) lacks active catechol 2,3-oxygenase; and
(c) does not grow on benzoate or monohalobenzoate; wherein the microbial culture is capable of metabolizing an aromatic substrate selected from toluene and other benzoic acid-precursors by the ortho pathway via catechol quantitatively to an accumulated quantity of muconic acid greater than about one gram per liter of a bioconversion medium.

2. Catechol 1,2-oxygenase in a microbial growth culture medium wherein the catechol, 1,2-oxygenase has activity that is not inhibited in the presence of less than about one gram per liter of muconic acid in the microbial culture growth medium, and wherein the microbial culture growth medium is capable of metabolizing an aromatic substrate selected from toluene and other benzoic acid-precursors by the ortho pathway via catechol quantitatively to an accumulated quantity of muconic acid greater than about one gram per liter of microbial culture growth medium.

* * * * *